United States Patent [19]

Staubli et al.

[11] Patent Number: 5,064,373
[45] Date of Patent: Nov. 12, 1991

[54] PLUG FORMING REMOVABLE CLOSURE IN OPENINGS OF DENTAL APPLIANCES AND THE LIKE

[75] Inventors: Peter E. Staubli, San Carlos, Calif.; Edgar K. Staubli, Zurich, Switzerland

[73] Assignee: Attachments International, Inc., San Mateo, Calif.

[21] Appl. No.: 429,756

[22] Filed: Oct. 31, 1989

[51] Int. Cl.$^5$ .............................................. A61C 8/00
[52] U.S. Cl. ..................................... 433/173; 433/220
[58] Field of Search ............... 433/167, 171, 172, 173, 433/174, 220, 221

[56] References Cited

U.S. PATENT DOCUMENTS

| | | | |
|---|---|---|---|
| 571,556 | 11/1896 | Comer | 433/172 |
| 744,291 | 11/1903 | Carr | 433/172 X |
| 4,177,562 | 12/1979 | Miller et al. | 433/174 |
| 4,182,034 | 1/1980 | McCauley | 433/174 |
| 4,793,808 | 12/1988 | Kirsch | 433/173 |
| 4,854,872 | 8/1989 | Detsch | 433/173 |
| 4,907,969 | 3/1990 | Ward | 433/173 |

FOREIGN PATENT DOCUMENTS 231838 8/1987 European Pat. Off. ............ 433/173
2516784 5/1983 France ............................. 433/173

Primary Examiner—Robert P. Swiatek
Assistant Examiner—Nicholas D. Lucchesi
Attorney, Agent, or Firm—John A. Bucher

[57] ABSTRACT

A plug and method of its use are disclosed for forming a removable closure in openings of dental appliances or other physiological appliances, the plug including an elongated shaft portion having a diameter mating with the opening, and an inner or gingival end of the plug which is enlarged by up to about 5%, more preferably about 1–5% and most preferably about 1–2% relative to the elongated shaft portion, the enlarged gingival plug end being an annulus having a radial thickness of up to about 20% and more preferably about 11% of the diameter of the enlarged plug end, the enlarged plug and the thickness of the annulus being selected together with the shaft material, preferably a resilient elastomer, to produce a cork type or press-fit engagement of the enlarged plug end in the appliance opening to retain the plug firmly in place. Preferably, the enlarged plug portion and the elongated shaft portion of the plug are integrally formed from a material permitting the shaft portion to be terminated relative to and preferably flush with the outer end of the opening.

25 Claims, 1 Drawing Sheet

PLUG FORMING REMOVABLE CLOSURE IN OPENINGS OF DENTAL APPLIANCES AND THE LIKE

FIELD OF THE INVENTION

The present invention relates to a plug and method of use for forming a closure in physiological appliance openings and more particularly to such a plug and method of use for forming a closure in occlusal/lingual openings of dental appliances such as artificial teeth or dentures.

BACKGROUND OF THE INVENTION

In a variety of physiological applications, particularly dentistry, appliances are provided as fixed detachable components on the human body, usually mounted by means of one or more screws attached to a bony substrate. For example, dental applications commonly employ such appliances in the form of fixed artificial teeth, bridges, dentures and the like which are also detachable or removable. More broadly, such appliances may also take a variety of forms such as other physical features of the human body, particularly in connection with maxiofacial restoration where eyes, ears, noses, cheeks, etc. are removable attached to underlying structures.

In attaching such appliances to the underlying substrate, an axial opening (relative to the longitudinal axis of the artificial tooth, etc.) is normally formed in the appliances for receiving each screw. After the appliance has been secured in place, it is then necessary to close the axial opening.

Dental appliances such as those noted above are commonly formed with an abutment forming an outwardly opening recess of uniform diameter. Depending upon the application, the abutment may also be termed a waxing sleeve, sleeve, coping, etc. Regardless of the nomenclature, the invention particularly contemplates such an appliance wherein an opening recess is formed for receiving a screw or other attachment device.

In typical processes, particularly for dental applications, a plastic abutment is employed to form a mold cavity prior to casting of the actual appliance. Such processes are well known to those skilled in the art and are not described in further detail herein. In any event, where the abutment formed from plastic, elastomer or other material is used to form an impression or mold cavity, the abutment is then commonly "burned out" and replaced by a metal abutment means during the casting process. The metal abutment means may be formed from an alloy of gold with another metal or by titanium, for example. Thereafter, a reamer or similar tool is then commonly used to accurately form a uniform diameter along the length of the opening.

In dental applications, appliances such as teeth, dentures, etc. are formed with such openings which extend inwardly to a gingival end adjacent tissue surrounding the appliance. The outer end of the opening is commonly termed an occlusal end for posterior teeth or a lingual end for anterior teeth.

Accordingly, to cover both types of such appliances, the opening is referred to herein as an occlusal/lingual opening having an inner or gingival end and an outer or occlusal/lingual end.

In employing such appliances in dentistry, it has been common practice to employ amalgams, plastics, resins, etc. in a workable condition to form a plug in each occlusal/lingual opening. This process is relatively time consuming in that a period of as long as five minutes, for example, may be required to form each plug in such an appliance.

Of equal or even greater concern in the prior art, these plugs were difficult to remove and it was often necessary to drill out the plug material, often resulting in fracture or damage to the appliance.

SUMMARY OF THE INVENTION

Accordingly, there has been found to exist a need for improved plugs for forming closures in such appliances which are capable of rapid installation and preferably also facilitate removal of the plug when necessary. In dental applications, for example, such a plug is of benefit both to the dentist and the patient because of the rapid installation. However, it is further necessary to assure that the plug remains securely in place within the opening until it is necessary or desirable to remove the plug, for example, either to repair or replace the appliance.

It is therefore an object of the invention to provide a plug and method of using such a plug for rapid installation to form an removable closure in occlusal/lingual openings for dental appliances such as artificial teeth, dentures, etc. and for other physiological appliances characterized by similar axial openings.

It is a further object of the invention to provide such a plug which is adapted for rapid installation to form a removable closure in occlusal/lingual openings of such dental appliances, the plug including an elongated shaft portion having a diameter mating with the diameter of the occlusal/lingual opening and an enlarged inner or gingival end of the plug which is an annulus having an axial opening therein, the size of the enlarged end of the plug and the thickness of the annulus being selected together with the shaft material in order to produce a cork type or press-fit engagement of the enlarged plug end within the opening in order to securely retain the plug in place. Preferably, the enlarged plug and the elongated shaft portion of the plug are integrally formed from a resilient elastomeric material contributing to the cork type or press-fit engagement of the plug within the opening while also permitting the elongated shaft portion to be terminated relative to and preferably flush with the outer end of the opening.

It is a further object to provide such a plug wherein the enlarged plug end is substantially shorter than the opening in order to ensure engagement of a portion of the elongated shaft within the opening.

Preferably, the enlarged plug end is up to about 5% larger than the elongated shaft, more preferably in the range of about 1-5% and even more preferably in the range of about 1-2% larger than the elongated shaft.

The annulus preferably has a radial thickness up to about 20% and more preferably about 11% of the diameter of the enlarged plug end.

It is a related object of the invention to provide a method of rapidly forming a removable closure for an axial opening in dental appliances, the method including the steps of forming the plug as noted above, inserting the plug into the opening and then terminating the elongated shaft relative to the outer end of the opening.

It is yet a further object of the invention to provide such a plug and method of use for the plug in connection with a variety of physiological appliances as noted above.

DESCRIPTION OF THE PREFERRED EMBODIMENT

As noted above, the present invention relates to a plug and method of use for the plug to rapidly form a closure for an opening in physiological appliances commonly provided as fixed detachable parts for the human body. As was also noted above, such appliances are usually mounted by means of a screw attaching to bony substrate in a portion of the body.

The invention more particularly contemplates a maxiofacial restoration appliance and even more preferably appliances for dental applications including artificial teeth, dentures, bridges, etc. In such appliances, the opening to be closed normally extends along the axis of the artificial tooth or other appliance. However, it will be apparent that the plug of the present invention may also be employed to form closures for openings otherwise oriented within the appliance.

Figure 1:
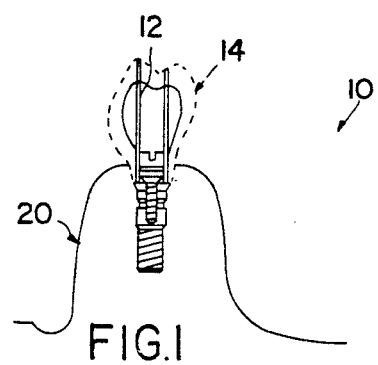
FIGS. 1 and 2 represent conventional steps in employing an abutment to mold a dental appliance such as a fixed removable artificial tooth illustrated in FIG. 2, the artificial tooth being secured in place to the bony substrate of the jaw by a screw inserted through an occlusal/lingual opening as illustrated in FIG. 2.
Figure 2:
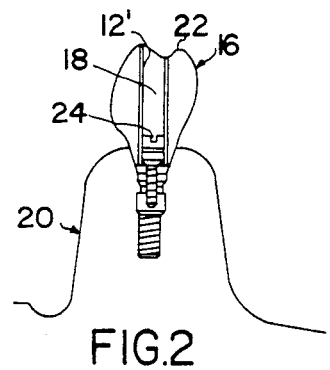

An appliance of the type contemplated by the present invention is illustrated in FIGS. 1 and 2. FIG. 1 generally illustrates a casting assembly 10 wherein a plastic or elastomeric abutment 12 is mounted as a base for forming a model 14 of an appliance or artificial tooth indicated at 16 in FIG. 2.

As noted above, the method of forming artificial teeth or other appliances is well known to those skilled in the art and is accordingly not described in great detail herein. For purposes of the present invention, it is sufficient to understand that during preparation or formation of the artificial tooth 16 of FIG. 2, the plastic abutment 12 of FIG. 1 is replaced by a hard metal abutment means 12' in the artificial tooth 16 of FIG. 2.

Furthermore, it is noted that the particular artificial tooth illustrated in FIG. 2 is of a posterior type with the metallic abutment 12' forming an opening 18 extending axially through the tooth 16 from a gingival area 20 toward an occlusal area 22 on the tooth. As noted above, if the artificial tooth were an anterior tooth, the opening would extend upwardly toward a lingual surface (not shown). In any event, to facilitate an understanding of the invention, the opening 18 is referred to herein as an occlusal/lingual opening to cover both types of teeth.

Once the opening 18 is formed in such an appliance, it is then commonly reamed or otherwise conditioned to have a uniform diameter along its length.

The plug of the present invention and its method of use are adapted for rapidly forming a removable closure in the occlusal/lingual opening or in other similar appliance openings. Referring again to FIG. 2, the artificial tooth 16 is secured in place by means of a screw 24 extending downwardly from the occlusal/lingual opening 18. Thus, the plug of the present invention is intended to perform a number of functions including sealing of the occlusal/lingual opening to prevent the screw from unthreading and at the same time to fill the occlusal/lingual opening without the need for conventional stuffing cotton, curing amalgam, composite or other conventional materials. At the same time that the plug is adapted for rapid installation to assure that it remains in place within the opening, it is also adapted for removal from the opening when necessary or desirable, for example, to facilitate removal, repair or replacement of the artificial tooth 16.

Figure 5:
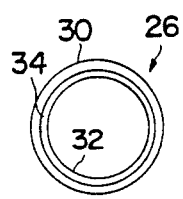
FIG. 5 is a view of the plug taken from the left end of FIG. 4.
Figure 4:
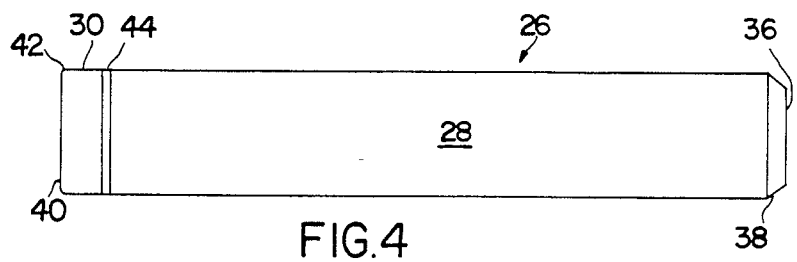
FIG. 4 is a side view of the plug.
Figure 3:
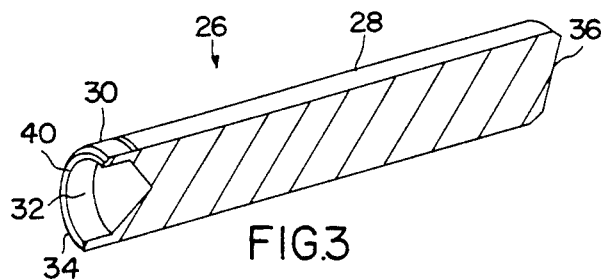
FIG. 3 is a pictorial and longitudinally sectioned view of a plug constructed in accordance with the present invention for use in forming a closure for the occlusal/lingual opening of a dental appliance as illustrated in FIG. 2.
Figure 6:
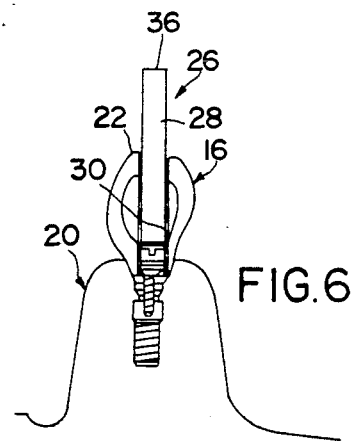
FIG. 6 illustrates the initial method of use for the plug which is then inserted into the occlusal/lingual opening of the artificial tooth of FIG. 2.

The plug of the present invention is illustrated at 26 in FIGS. 3-5 and includes an elongated shaft portion 28 having a uniform diameter closely mating with the diameter of the occlusal/lingual opening 18 (see FIG. 2). Accordingly, the invention contemplates a series of plugs respectively sized for openings in different appliances.

The plug 26 also includes an enlarged inner or gingival end 30 contemplated for initial insertion into the occlusal/lingual opening 18. The enlarged plug end 30 has a diameter slightly greater than the diameter of the elongated shaft portion 28 and is further formed with an axial opening 32 forming an annulus 34 extending through the axial length of the enlarged plug end 30.

In accordance with the present invention, the enlarged diameter of the plug end 30, the thickness of the annulus 34, the length of the opening 30 and the material from which the plug, specifically the plug end 30, is formed are selected together in order to assure a cork type or press-fit engagement of the enlarged plug end 30 within the occlusal/lingual opening 18.

Preferably, the enlarged plug end 30 and the elongated shaft portion 28 of the plug are integrally formed from a resilient elastomeric material. The elastomeric material is selected not only to contribute to the cork type or press-fit engagement as described above but also to facilitate termination of the elongated shaft portion 28 generally adjacent the outer end of the opening 18. In most applications, the elongated shaft portion 28 is terminated generally flush with the occlusal or outer surface 22 of the tooth or appliance so that it does not interfere with use of the tooth but completely fills the occlusal/lingual opening 18.

Suitable elastomeric materials for forming the plug 26 include polyethylenes (such as those available under the trademark DELRIN), nylons (such as those available under the trade names ZYTEL and NYTEL) and ABS (acrylic-butadiene-styrene) polymers and other polymers having generally similar characteristics, these materials for the plug also serving to define the degree of resilience required particularly in the enlarged plug end 30 in accordance with the preceding discussion.

It is also important that the length of the plug 26, particularly the length of the enlarged plug end 30, be selected with reference to the particular occlusal/lingual opening 18 in order to assure that the plug is securely positioned within the opening. Alternatively, it may also be considered necessary to assure that the occlusal/lingual opening 18 or other similar appliance opening has a sufficient length to accommodate the plug 26 for this purpose.

Figure 7:
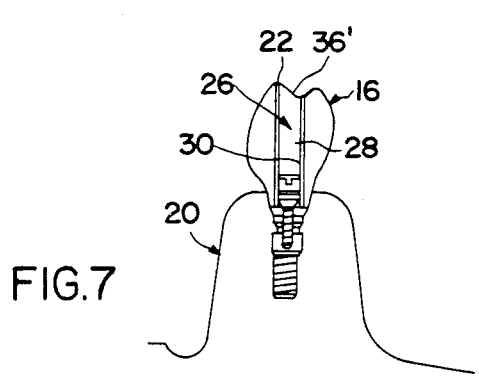
FIG. 7 illustrates the same combination of the artificial tooth and plug as in FIG. 6 but with an end of the plug extending from the outer or occlusal end of the opening being terminated generally flush therewith.

In any event, it is necessary that the enlarged gingival or inner plug end 30 be substantially shorter than the overall length of the occlusal/lingual opening so that a substantial portion of the elongated shaft portion 28 is also in engagement with the opening 18. Preferably, the enlarged inner plug end 30 is no more than generally about one half the axial length of the opening 18 from the top of the screw 24 to the occlusal surface 22. More preferably, as illustrated in FIG. 7, the enlarged inner plug end 30 has an axial length about one tenth of the axial length of the opening 18.

Different appliances such as the artificial tooth 16 of FIG. 2 may have appliance openings in a variety of diameters and lengths. Only for purposes of example, the artificial tooth 16 may typically have an occlusal/lingual opening 18 which is approximately 0.098 inches in diameter and a length, from the top of the screw 24 to the occlusal surface 22 of about 0.25 inches. These dimensions are provided only for the purpose of facilitating a discussion of exemplary dimensions for the plug 26 of the invention.

For an appliance as described immediately above, the plug would have a diameter for its elongated shaft portion 28 mating with the diameter of the occlusal/lingual opening 18, that is approximately 0.098 inches in diameter.

In accordance with the present invention, the diameter of the enlarged plug end 30 is up to about 5% greater than the diameter of the enlarged shaft portion 28, preferably in the range of about 1-5% and more preferably in the range of about 1-2%. For the particular appliance or artificial tooth with dimensions as noted above, the elongated shaft portion 28 would have a diameter of 0.098 inches with the enlarged plug end 30 having a diameter of 0.099 inches. Because of the precise dimensions necessary for the plug, it has also been found generally unfeasible to produce the plug by casting. Precision techniques such as machining have been found necessary in order to assure proper dimensions of the plug, particularly in the diameter of the shaft portion 28 and enlarged plug end 30.

The plug 26 is initially formed with the elongated shaft portion 28 several times longer than the length of the enlarged inner plug end 30. The elongated shaft portion 28 must be at least one or two times longer than the enlarged plug end 30 in order to assure proper engagement within the opening 18 as described above. For the appliance or artificial tooth with the dimensions noted above, the plug may have exemplary dimensions including an overall length of about 0.56 inches with the enlarged plug end 30 having a length of about 0.04 inches. The outer or occlusal/lingual end 36 of the plug 26 is formed with a beveled surface 38, preferably about 30 degrees relative to the cylindrical surface of the elongated shaft portion 28. Similarly, the inner or gingival end 40 of the enlarged plug end 30 is also formed with a beveled surface 42, preferably about 45 degrees relative to the cylindrical surface of the enlarged plug end 30. Preferably, a similar bevel or taper is also formed at 44 as a transition between the enlarged plug end 30 and the elongated shaft portion 28.

The axial opening 32 preferably extends entirely through the enlarged plug end 30 in order to assure the desired cork type or press-fit engagement discussed above. As illustrated in FIG. 4, the axial opening 32 is counterbored with a tapered portion of the counterbore extending past the enlarged plug end 30.

To further assure a proper engagement between the enlarged plug end 30 and the opening 18, the annulus 34 preferably has a radial dimension of no more than about 20% of the overall diameter of the enlarged plug end 30. Similarly, the radial thickness of the annulus 34 is preferably no less than about 7.5% of the diameter of the enlarged plug end 30. Preferably, the radial thickness of the annulus 34 is about 10% and more specifically about 11% of the diameter of the enlarged plug end 30. For the exemplary dimensions noted above the counterbored axial opening 32 thus has a diameter of about 0.078 inches so that the radial thickness of the annulus 34 is approximately 11% of the diameter for the enlarged plug end 30.

With the materials and dimensions formed in accordance with the parameters noted above, the enlarged plug end 30 of the plug 26 may then be readily inserted under some force into the occlusal/lingual opening 18. The enlarged plug end 30 penetrates into the opening 18 closely adjacent the screw 24 and assures engagement of the plug within the opening. Since the elongated shaft portion 28 has a diameter mating with the opening 18, it completely fills the opening throughout its length.

Because of the materials selected for the plug, the elongated shaft portion 28 may then be terminated, preferably by cutting, adjacent the outer or occlusal surface 22 of the artificial tooth 16 (see FIG. 2).

A method of use for a plug constructed according to the present invention is believed clearly apparent from the preceding description. However, the method of use for the plug is described briefly below in order to assure a complete understanding of the invention.

Initially, the plug is formed in accordance with the preceding description to have an elongated shaft portion 28 and enlarged plug end 30 with dimensions as described above and formed from a suitable material as described above.

With an appliance such as the artificial tooth 16 of FIG. 2 being completed and secured in place by means of the screw 24, the plug 26 is then inserted into the occlusal/lingual opening, 18 so that the enlarged inner plug end 30 penetrates the opening adjacent the screw. With the enlarged plug end 30 firmly secured within the opening 18, the elongated shaft portion 28 is then preferably terminated generally adjacent the outer end or occlusal surface 22 of the opening 18. More preferably, the elongated shaft portion 28 is cut or severed generally flush with the occlusal surface 22 for esthetic purposes and also to assure that it does not interfere with proper functioning of the tooth. At the same time, the plug remains securely in place within the opening 18 while being capable of removal when desired or necessary as noted above. For example, the plug may be removed, for example, by drilling into the outer or occlusal end of the elongated shaft portion 28 with a burr. The polymer in the plug tends to build up on the burr and bind it to the plug so that the burr and plug can be withdrawn together from the opening 18 without damaging the opening 18 or the surrounding material of the artificial tooth or appliance 16.

Accordingly there has been described above an effective plug and method of its use permitting rapid installation of a removable closure for openings in appliances such as an occlusal/lingual opening in a dental appliance.

Numerous modifications will be apparent in addition to those specifically noted above. Accordingly, the scope of the present invention is defined only by the following claims which are also set forth a further examples of the invention.

What is claimed is:

1. A plug for use with dental appliances, the plug being adapted for rapid installation to form a removable closure in occlusal/lingual openings of dental appliances such as artificial teeth or dentures, the occlusal/lingual opening having a substantially uniform diameter with an inner or gingival end and an outer or occlusal/lingual end, the plug comprising an elongated shaft portion having a diameter selected to mate with the diameter of the occlusal/lingual opening, and an inner or gingival end of the plug which is enlarged relative to the elongated shaft portion, the enlarged gingival plug end being an annulus with an axial opening extending within the plug to a junction of the inner or gingival plug end and the elongated shaft portion, the shaft portion being solid, the relative enlargement of the gingival plug end and the thickness of the annulus being selected together with the shaft material to develop a cork type or press-fit engagement of the enlarged gingival plug end with the occlusal/lingual opening in order to retain the plug firmly in place within the occlusal/lingual opening.

2. The plug of claim 1 wherein the enlarged gingival plug end and the elongated shaft portion of the plug are integrally formed from a resilient elastomeric material contributing to the cork type or press-fit engagement of the plug within the occlusal/lingual opening while also permitting the elongated shaft portion to be terminated relative to the outer or occlusal/lingual end of the occlusal/lingual opening.

3. The plug of claim 2 wherein the enlarged gingival plug end is substantially shorter than the length of the occlusal/lingual opening to ensure engagement of a portion of the elongated shaft with the occlusal/lingual opening.

4. The plug of claim 1 wherein the enlarged gingival plug end is substantially shorter than the length of the occlusal/lingual opening to ensure engagement of a portion of the elongated shaft with the occlusal/lingual opening.

5. The plug of claim 4 wherein the enlarged gingival plug end is up to about 5% diametrically larger than the elongated shaft.

6. The plug of claim 5 wherein the enlarged gingival plug end is in the range of about 1-5% diametrically larger than the elongated shaft.

7. The plug of claim 5 wherein the enlarged gingival plug end is in the range of about 1-2% diametrically larger than the elongated shaft.

8. The plug of claim 7 wherein the annulus has a radial thickness of up to about 20% of the diameter of the enlarged gingival plug end.

9. The plug of claim 8 wherein the annulus has a radial thickness of up to about 11% of the diameter of the enlarged gingival plug end.

10. The plug of claim 5 wherein the annulus has a radial thickness of up to about 20% of the diameter of the enlarged gingival plug end.

11. The plug of claim 1 wherein the annulus has a radial thickness of up to about 20% of the diameter of the enlarged gingival plug end.

12. The plug of claim 11 wherein the annulus has a radial thickness of up to about 11% of the diameter of the enlarged gingival plug end.

13. A method of rapidly forming a removable closure for an occlusal/lingual opening in a dental appliance such as an artificial tooth or denture, the occlusal/lingual opening having a substantially uniform diameter with an inner or gingival end and an outer or occlusal/lingual end, comprising the steps of forming a plug to include an elongated shaft portion having a diameter selected to mate with the diameter of the occlusal/lingual opening, and an inner or gingival end of the plug which is enlarged relative to the elongated shaft portion, the enlarged gingival plug end being an annulus with an axial opening extending within the plug to a junction of the inner or gingival plug end and the elongated shaft portion, the shaft portion being solid, the relative enlargement of the gingival plug end and the thickness of the annulus being selected together with the shaft material to produce a cork type or press-fit engagement of the enlarged gingival plug end with the occlusal/lingual opening to retain the plug firmly in place within the occlusal/lingual opening, inserting the plug into the occlusal/lingual opening, and terminating the elongated shaft relative to the outer or occlusal/lingual end of the occlusal/lingual opening.

14. The method of claim 13 wherein the enlarged gingival plug end and the elongated shaft portion of the plug are integrally formed from a resilient elastomeric material contributing to the cork type or press-fit engagement of the plug within the occlusal/lingual opening while also permitting the elongated shaft portion to be terminated relative to the outer or occlusal/lingual end of the occlusal/lingual opening.

15. The method of claim 14 wherein the enlarged gingival plug end is substantially shorter than the length of the occlusal/lingual opening to ensure engagement of a portion of the elongated shaft with the occlusal/lingual opening.

16. The method of claim 15 wherein the enlarged gingival plug end is in the range of about 1-5% diametrically larger than the elongated shaft.

17. The method of claim 16 wherein the annulus has a radial thickness of up to about 20% of the diameter of the enlarged gingival plug end.

18. A plug for use with dental appliances, the plug being adapted for rapid installation to form a removable closure in openings of physiological appliances, the openings having substantially uniform diameter with an inner end and an outer end, the plug comprising an elongated shaft portion having a diameter selected to mater with the diameter of the appliance opening, and an inner or gingival end of the plug which is enlarged relative to the elongated shaft portion, the enlarged inner plug end being an annulus with an axial opening extending within the plug to a junction of the inner or gingival plug end and the elongated shaft portion, the shaft portion being solid, the relative enlargement of the inner plug end and the thickness of the annulus being selected together with the shaft material to produce a cork type or press-fit engagement of the enlarged inner plug end with the appliance opening to retain the plug firmly in place within the appliance opening.

19. The plug of claim 18 wherein the enlarged inner plug end and the elongated shaft portion of the plug are integrally formed from a resilient elastomeric material contributing to the cork type or press-fit engagement of the plug within the appliance opening while also permitting the elongated shaft portion to be terminated relative to the outer end of the appliance opening.

20. The plug of claim 19 wherein the enlarged inner plug end is substantially shorter than the length of the appliance opening to ensure engagement of a portion of the elongated shaft with the appliance opening.

21. The plug of claim 20 wherein the enlarged inner plug end is up to about 5% diametrically larger than the elongated shaft.

22. The plug of claim 21 wherein the annulus has a radial thickness of up to about 20% of the diameter of the enlarged inner plug end.

23. A method of rapidly forming a removable closure for an appliance opening in physiological appliances, the appliance opening having a substantially uniform diameter with an inner end and an outer end, comprising the steps of forming a plug to include an elongated shaft portion having a diameter mating with the diameter of the appliance opening, and an inner end of the plug which is enlarged relative to the elongated shaft portion, the enlarged inner plug end being an annulus with an axial opening extending within the plug to a junction of the inner or gingival plug end and the elongated shaft portion, the shaft portion being solid, the relative enlargement of the inner plug end and the thickness of the annulus being selected together with the shaft material to produce a cork type or press-fit engagement of the enlarged plug end with the appliance opening to retain the plug firmly in place within the appliance opening, inserting the plug into the appliance opening, and terminating the elongated shaft relative to the outer end of the appliance opening.

24. The method of claim 23 wherein the enlarged gingival plug end and the elongated shaft portion of the plug are integrally formed from a resilient elastomeric material contributing to the cork type or press-fit engagement of the plug within the opening while also permitting the elongated shaft portion to be terminated relative to the outer end of the opening.

25. The method of claim 24 wherein the enlarged gingival plug end is substantially shorter than the length of the occlusal/lingual opening to ensure engagement of a portion of the elongated shaft with the opening.

* * * * *